United States Patent [19]
Baker et al.

[11] Patent Number: 5,153,199
[45] Date of Patent: Oct. 6, 1992

[54] FUNGICIDAL COMPOUNDS

[75] Inventors: Don R. Baker, Orinda, Calif.; Patrick J. Crowley, Crowthorne, England; Paul A. Worthington, Maidenhead, England; Ian R. Matthews, Wokingham, England

[73] Assignee: Imperial Chemical Industries PLC, London, United Kingdom

[21] Appl. No.: 631,299

[22] Filed: Dec. 19, 1990

[30] Foreign Application Priority Data

Dec. 22, 1989 [GB] United Kingdom ............... 8929019
May 3, 1990 [GB] United Kingdom ............... 9010033

[51] Int. Cl.$^5$ ............... A01N 43/60; C07D 211/00; C07D 239/02
[52] U.S. Cl. ............... 514/255; 514/256; 514/269; 514/332; 514/335; 514/341; 514/343; 514/349; 514/352; 544/242; 544/333; 544/334; 544/335; 544/405; 546/255; 546/261; 546/265; 546/268; 546/278; 546/281; 546/283; 546/284; 546/290; 546/297; 546/309
[58] Field of Search ............... 546/309, 297, 258, 261, 546/265, 268, 278, 281, 283, 284, 290; 544/242, 333, 334, 335, 405; 514/255, 256, 269, 332, 335, 341, 343, 349, 352

[56] References Cited

U.S. PATENT DOCUMENTS

| | | | |
|---|---|---|---|
| 4,766,134 | 8/1988 | Baker et al. | 514/346 |
| 4,766,135 | 8/1988 | Baker et al. | 546/261 |
| 4,767,771 | 8/1988 | Baker et al. | 546/297 |
| 4,767,772 | 8/1988 | Baker et al. | 546/283 |
| 4,797,407 | 1/1989 | Baker et al. | 546/283 |
| 4,800,205 | 1/1989 | Baker et al. | 546/292 |
| 4,808,600 | 2/1989 | Baker et al. | 546/292 |
| 4,824,854 | 4/1989 | Baker et al. | 546/297 |
| 4,831,044 | 5/1989 | Baker et al. | 546/283 |
| 4,845,107 | 7/1989 | Baker et al. | 546/292 |
| 4,894,379 | 1/1990 | Baker et al. | 546/292 |
| 4,895,858 | 1/1990 | Baker et al. | 514/346 |
| 4,914,115 | 4/1990 | Baker et al. | 546/292 |
| 4,931,451 | 6/1990 | Baker et al. | 514/335 |
| 4,975,442 | 12/1990 | Baker et al. | 546/291 |
| 4,975,443 | 12/1990 | Baker et al. | 546/292 |
| 4,977,164 | 12/1990 | Baker et al. | 546/292 |
| 4,992,503 | 2/1991 | Baker et al. | 546/292 |

Primary Examiner—C. Warren Ivy
Assistant Examiner—Raymond Covington
Attorney, Agent, or Firm—Michael J. Bradley

[57] ABSTRACT

Compounds having the general formula (I):

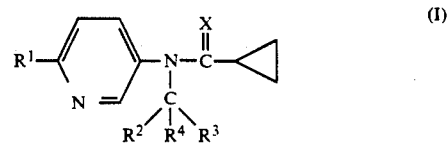

and optical isomers thereof, wherein X is oxygen or sulphur; $R^1$ is halogen, $C_{1-4}$ alkoxy or $C_{1-4}$ haloalkoxy; $R^2$ and $R^3$, which are the same or different, are hydrogen, $-CO_2R^5$ or $C_{1-4}$ alkyl; $R^4$ is hydrogen, cyano, $C_{1-4}$ alkyl (optionally substituted with cyano or halogen), $-(CH_2)_nCO_2R^6$, $-CONR^6R^7$, $C_{3-6}$ cycloalkyl, $C_{2-4}$ alkenyl, $C_{2-4}$ alkynyl, optionally substituted phenyl or optionally substituted heteroaromatic; or the group $CR^2R^3R^4$ can form an allene moiety optionally substituted with $C_{1-4}$ alkyl; $R^5$, $R^6$ and $R^7$, which are the same or different, are hydrogen or $C_{1-4}$ alkyl; n is 0, 1, 2, 3 or 4; and metal complexes thereof are active as fungicides.

7 Claims, No Drawings

FUNGICIDAL COMPOUNDS

The present invention relates to pyridyl cyclopropane amide derivatives that are useful as fungicides, to processes for preparing them, to fungicidal compositions containing them, and to methods of using them to combat fungi, especially fungal infections of plants.

According to the present invention there is provided a compound having the general formula (I):

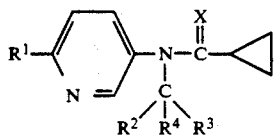

and optical isomers thereof, wherein X is oxygen or sulphur; $R^1$ is halogen, $C_{1-4}$ alkoxy or $C_{1-4}$ haloalkoxy; $R^2$ and $R^3$, which are the same or different, are hydrogen, $-CO_2R^5$ or $C_{1-4}$ alkyl; $R^4$ is hydrogen, cyano, $C_{1-4}$ alkyl optionally substituted with cyano or halogen), $-(CH_2)_nCO_2R^6$, $-CONR^6R^7$, $C_{3-6}$ cycloalkyl, $C_{2-4}$ alkenyl, $C_{2-4}$ alkynyl, optionally substituted phenyl or optionally substituted heteroaromatic; or the group $CR^2R^3R^4$ can form an allene moiety optionally substituted with $C_{1-4}$ alkyl; $R^5$, $R^6$ and $R^7$, which are the same or different, are hydrogen or $C_{1-4}$ alkyl; n is 0, 1, 2, 3 or 4; and metal complexes thereof.

The compounds of the invention exist as optical isomers when $R^2$, $R^3$ and $R^4$ are all different. Such isomers and mixtures thereof in all proportions constitute a part of the present invention.

Halogen includes fluorine, chlorine, bromine and iodine.

Alkyl groups and the alkyl moiety of the alkoxy group contain 1 to 4 carbon atoms and are in the form of either straight or branched chains, i.e. methyl, ethyl, n-propyl, iso-propyl, n-butyl, iso-butyl, sec-butyl or tert-butyl.

The haloalkoxy group contains from 1 to 4 carbon atoms and at least one halogen atom. It is in the form of either a straight or branched chain and is, for example, halomethoxy, haloethoxy, halopropyloxy or halobutoxy in which the halogen is fluorine, chlorine, bromine or iodine.

The cycloalkyl group contains from 3 to 6 carbon atoms, and is, for example, cyclopropyl or cyclohexyl.

The alkenyl group contains from 2 to 4 carbon atoms and is, for example, vinyl or allyl.

The alkynyl group contains from 2 to 4 carbon atoms and is, for example, ethynyl, 1-propynyl or 2-propynyl.

The heteroaromatic group is preferably a 5- or 6-membered ring containing one or more nitrogen, sulphur or oxygen atoms The heteroaromatic group is, for example, pyridine, furan, thiophene or pyrimidine Optional substituents on the phenyl and heteroaromatic moieties include $C_{1-4}$ alkyl, $C_{1-4}$ haloalkyl, $C_{1-4}$ alkoxy, $C_{1-4}$ haloalkoxy, $C_{1-4}$ alkoxy($C_{1-4}$)alkyl, halogen, nitro, cyano, amino, mono- or di-($C_{1-4}$)alkylamino, , $CO_2R^8$, $COR^8$, $SO_2R^9$ and hydroxy; $R^8$ is hydrogen, $C_{1-4}$ alkyl, $C_{1-4}$ haloalkyl or phenyl optionally substituted with halogen, $C_{1-4}$ alkyl, $C_{1-4}$ haloalkyl, $C_{1-4}$ alkoxy or $C_{1-4}$ haloalkoxy; $R^9$ is $C_{1-4}$ alkyl, $C_{1-4}$ haloalkyl or phenyl optionally substituted with halogen, $C_{1-4}$ alkyl, $C_{1-4}$ haloalkyl, $C_{1-4}$ alkoxy or $C_{1-4}$ haloalkoxy.

In one particular aspect the present invention provides compounds of general formula (I):

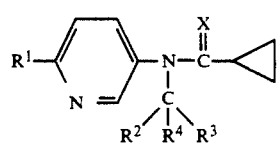

wherein X is oxygen or sulphur; $R^1$ is halogen, $C_{1-4}$ alkoxy or $C_{1-4}$ haloalkoxy; $R^2$ and $R^3$ are both hydrogen; $R^4$ is hydrogen, cyano, $C_{1-4}$ alkyl (optionally substituted with cyano or halogen), $C_{3-6}$ cycloalkyl, $C_{2-4}$ alkenyl or $C_{2-4}$ alkynyl; or the group $CR^2R^3R^4$ can form an allene moiety optionally substituted with $C_{1-4}$ alkyl.

In a further aspect the present invention provides compounds of general formula (I):

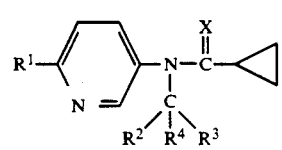

wherein X is oxygen or sulphur; $R^1$ is halogen (preferably chlorine or fluorine) or $C_{1-4}$ alkoxy (especially methoxy); $R^2$ and $R^3$ are both hydrogen; and $R^4$ is hydrogen, cyano, $C_{1-4}$ alkyl (optionally substituted with cyano or halogen), $C_{2-4}$ alkenyl (especially vinyl) or $C_{2-4}$ alkynyl (especially ethynyl and prop-1-ynyl).

In a still further aspect the present invention provides compounds of general formula (I):

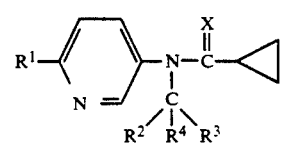

wherein X is oxygen; $R^1$ is $C_{1-4}$ alkoxy (especially methoxy); $R^2$ and $R^3$ are both hydrogen; and $R^4$ is hydrogen, cyano, $C_1$ alkyl (optionally substituted with cyano or halogen), $C_{2-4}$ alkenyl (especially vinyl) or $C_{2-4}$ alkynyl (especially ethynyl and prop-1-ynyl).

In another aspect the present invention provides compounds of general formula (I):

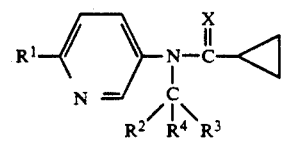

wherein X is oxygen; $R^1$ is methoxy; $R^2$ and $R^3$ are hydrogen; and $R^4$ is hydrogen, cyano, $C_{1-2}$ alkyl (optionally substituted by fluorine or cyano), vinyl, ethynyl or prop-1-ynyl.

In still a further aspect the present invention provides compounds of formula (I) in which $R^1$ is $C_{1-4}$ alkoxy (especially methoxy) or halogen (especially fluorine or chlorine); $R^2$ is hydrogen; $R^3$ is hydrogen, methyl or $-CO_2CH_3$; and $R^4$ is hydrogen, cyano, $C_{1-4}$ alkyl (especially methyl, ethyl or propyl), $C_{1-4}$ haloalkyl (especially fluoromethyl or difluoromethyl), —$CO_2C_{1-2}$ alkyl, —$CO_2NH_2$, $(CH_2)_nCO_2C_{1-2}$ alkyl (wherein n is 1 or 2), cyclopropyl, ethenyl, ethynyl, prop-1-ynyl, furyl, pyridyl or phenyl substituted with one or more of halogen (especially chlorine), nitro, cyano, $C_{1-4}$ haloalkyl (especially trifluoromethyl) or $C_{1-4}$ alkoxy (especially methoxy).

Examples of compounds (I) according to the invention are given in Tables I and II. In Tables I and II the significance of the abbreviations is as follows:
Me represents methyl
Et represents ethyl
nPr represents normal propyl
iPr represents iso propyl In Tables I and II selected proton NMR data are given for certain compounds. Where these data are given, chemical shifts are in ppm from tetramethylsilane and deuterochloroform was used as a solvent. The following abbreviations are used:
s = singlet
d = doublet
m = multiplet
dd = doublet of doublets
q = quartet
dt = doublet of triplets
tt = triplet of triplets
td = triplet of doublets In Table I melting points (mp) are given for certain compounds.

TABLE I (I)

| Compound No. | $R^1$ | $R^2$ | $R^3$ | $R^4$ | NMR/mp |
|---|---|---|---|---|---|
| 1 | MeO | H | H | H | 8.1(d, 1H); 7.5(dd, 1H); 6.8(d, 1H); 3.95(s, 3H); 3.3 (s, 3H); 1.35(m, 1H); 1.05 (m, 2H); 0.65(m, 2H). |
| 2 | MeO | Me | H | H | 8.1(d, 1H); 7.5(dd, 1H); 6.8 (d, 1H); 3.95(s, 3H); 3.75(q, 2H); 1.25(m, 1H); 1.1 (t, 3H); 1.0(m, 2H); 0.65(m, 2H). |
| 3 | MeO | Et | H | H | 8.1(d, 1H); 7.5(dd, 1H); 6.8 (d, 1H); 3.95(s,3H); 3.65 (t, 2H); 1.5(m, 2H); 1.25 (m, 1H); 1.0(m, 2H); 0.9 (t, 3H); 0.65(m, 2H). |
| 4 | MeO | $^n$Pr | H | H | 8.1(d, 1H); 7.5(dd, 1H); 6.8(d, 1H); 3.95 (s, 3H); 3.70(t, 2H); 1.5(m, 2H); 1.3(m, 3H); 1.0(m, 2H); 0.9(t, 3H); 0.65(m, 2H). |
| 5 | MeO | Me | Me | H | 81–85° C. |
| 6 | F | H | H | H | 8.2(m, 1H); 7.7(m, 1H); 7.0(dd, 1H); 3.3 (s, 3H); 1.3(m, 1H); 1.05(m, 2H); 0.7(m, 2H). |
| 7 | F | Me | H | H | 8.2(m, 1H); 7.7(m, 1H); 7.0(dd, 1H); 3.8 (q, 2H); 1.2(m, 4H); 1.05(m, 2H); 0.7(m, 2H). |
| 8 | F | Et | H | H | 8.2(m, 1H); 7.7(m, 1H); 7.0(dd, 1H); 3.7 (t, 2H); 1.5(m, 2H); 1.2(m, 1H); 1.05(m, 2H); 0.9(t, 3H); 0.7(m, 2H). |
| 9 | F | Me | Me | H | 69–73° C. |
| 10 | $^i$PrO | Me | Me | H | 8.0(d, 1H); 7.4(dd, 1H); 6.7(d, 1H); 5.3(m, 1H); 5.0(m, 1H); 1.4(s, 6H); 1.35(s, 6H); 0.8-1.3(m, 3H); 0.6(m, 2H). |
| 11 | F | H | H | 4-$NO_2$—$C_6H_4$ | 77–81° C. |
| 12 | F | H | H | 3,4-$Cl_2$—$C_6H_3$ | 8.03(d, 1H); 7.54(d, 1H); 7.35(d, 1H); 7.30 (d, 1H); 7.03(dd, 1H); 6.98(dd, 1H); 4.84 (s, 2H); 1.24(bs, 1H); 1.10(m, 2H); 0.73(m, 2H). |
| 13 | MeO | H | H | 2-$NO_2$—$C_6H_4$ | 8.00(d, 1H); 7.94 (d, 1H); 7.60(m, 2H); 7.44(m, 2H); 6.74 (d, 1H); 5.26(s, 2H); 3.91(s, 3H); 1.44(m, 1H); 1.09(m, 2H); 0.73(m, 2H). |
| 14 | MeO | H | H | 3-$NO_2$—$C_6H_4$ | 8.11(d, 1H); 8.05 (s, 1H); 7.94(d, 1H); |

TABLE I-continued (I)

$$R^1\text{-pyridine-N(C(=O)cyclopropyl)-C(R^2)(R^4)(R^3)}$$

| Compound No. | R¹ | R² | R³ | R⁴ | NMR/mp |
|---|---|---|---|---|---|
| | | | | | 7.63(d, 1H); 7.50 (t, 1H); 7.38(dd, 1H); 6.77(d, 1H); 4.99(s, 2H); 3.91(s, 3H); 1.37(m, 1H); 1.08(m, 2H); 0.73(m, 2H). |
| 15 | MeO | H | H | 4-CN—C₆H₄ | 7.91(d, 1H); 7.59 (d, 2H); 7.33(m, 3H); 6.75(d, 1H); 4.92 (s, 2H); 3.92(s, 3H); 1.34(m, 1H); 1.07 (m, 2H); 0.72(m, 2H). |
| 16 | MeO | H | H | 4-NO₂—C₆H₄ | 67–71° C. |
| 17 | F | H | H | ⁿPr | 8.2(m, 1H); 7.7(m, 1H); 7.05(dd, 1H); 3.7(t, 2H); 1.5(m, 2H); 1.1–1.4(m, 3H); 1.05(m, 2H); 0.9(t, 3H); 0.7(m, 2H). |
| 18 | MeO | H | H | —CO₂Et | |
| 19 | MeO | H | H | cyclopropyl | 8.1(d, 1H); 7.5(dd, 1H); 6.8(d, 1H); 4.0(s, 3H); 3.6(d, 2H); 1.3(m, 1H); 1.0(m, 2H); 0.95(m, 1H); 0.65(m, 2H); 0.45(m, 2H); 0.1(m, 2H). |
| 20 | MeO | H | H | —CONH₂ | 123–130° C. |
| 21 | MeO | H | H | —(CH₂)₂CO₂Et | |
| 22 | MeO | H | —CO₂Me | —CH₂CO₂Me | |
| 23 | MeO | H | H | CH=CH₂ | 8.1(d, 1H); 7.5(dd, 1H); 6.8(d, 1H); 5.7–6.0 (m, 1H); 5.0–5.2(m, 2H); 4.3(d, 2H); 3.95(s, 3H); 1.3(m, 1H); 1.0(m, 2H); 0.65(m, 2H). |
| 24 | MeO | H | H | C≡CH | 8.2(d, 1H); 7.6(dd, 1H); 6.8(d, 1H); 4.5(d, 2H); 3.95(s, 3H); 2.2(t, 1H); 1.3(m, 1H); 1.0(m, 2H); 0.7(m, 2H). |
| 25 | MeO | H | H | C≡CMe | 8.2(d, 1H); 7.6(dd, 1H); 6.8(d, 1H); 4.4(q, 2H); 3.95(s, 3H); 1.8(t, 3H); 1.3(m, 1H); 1.05(m, 2H); 0.65(m, 2H); |
| 26 | Cl | H | H | H | 8.4(d, 1H); 7.65(dd, 1H); 7.4(d, 1H); 3.3(s, 3H); 1.4(m, 1H); 1.1(m, 2H); 0.7(m, 2H). |
| 27 | Cl | H | H | Me | 8.35(d, 1H); 7.6(dd, 1H); 7.4(d, 1H); 3.8(q, 2H); 1.25(m, 1H); 1.1(t, 3H); 1.05(m, 2H); 0.7(m, 2H). |
| 28 | Cl | H | H | Et | 8.35(d, 1H); 7.6(dd, 1H); 7.4(d, 1H); 3.7(m, 2H); 1.5(m, 2H); 1.3(m, 1H); 1.05(m, 2H); 0.9(t, 3H); 0.7(m, 2H). |
| 29 | Cl | H | H | CH=CH₂ | 8.35(d, 1H); 7.6(dd, 1H); 7.4(d, 1H); 5.7–6.0(m, 1H); 5.0–5.2(m, 2H); 4.3(d, 2H); 1.3(m, 1H); 1.1(m, 2H); 0.7(m, 2H). |
| 30 | Cl | H | H | C≡CH | 8.45(d, 1H); 7.7(dd, 1H); 7.45(d, 1H); 4.5(d, 2H); 2.3(t, 1H); 1.3(m, 1H); 1.1(m, 1H); 0.75(m, 2H). |
| 31 | MeO | H | H | CH₂F | 8.15(d, 1H); 7.55(dd, 1H); 6.8(d, 1H); 4.6(dt, 2H); 4.0(s, 3H); 3.95(dt, 2H); 1.3(m, 1H); 1.0(m, 2H); 0.7(m, 2H). |
| 32 | MeO | H | H | CHF₂ | 8.1(d, 1H); 7.5(dd, 1H); 6.8(d, 1H); 6.1(tt, 1H); 4.0(s, 3H); 3.95(td, 2H); |

TABLE I-continued (I)

| Compound No. | R¹ | R² | R³ | R⁴ | NMR/mp |
|---|---|---|---|---|---|
| 33 | MeO | H | H | $^i$Pr | 1.3(m, 1H); 1.0(m, 2H); 0.7(m, 2H). 8.1(d, 1H); 7.5(dd, 1H); 6.8(d, 1H); 3.95(s, 3H); 3.5(d, 2H); 1.8(m, 1H); 1.3(m, 1H); 1.0(m, 2H); 0.9(d, 6H); 0.65(m, 2H). |
| 34 | MeO | H | H | CN | 84–87° C. |
| 35 | MeO | H | H | 4-CF₃—C₆H₄ | 7.9(d, 1H); 7.55(d, 2H); 7.3(m, 3H); 6.7(d, 1H); 4.9(s, 2H); 3.9(s, 3H); 1.3(m, 1H); 1.1(m, 2H); 0.7(m, 2H). |
| 36 | MeO | H | H | 3,4-(MeO)₂—C₆H₃ | 7.9(d, 1H); 7.2(dd, 1H); 6.7(m, 4H); 4.8(s, 2H); 3.9(s, 3H); 3.85(s, 3H); 3.8(s, 3H); 1.3(m, 1H); 1.1(m, 2H); 0.7(m, 2H). |
| 37 | MeO | H | H | fur-2-yl | 7.95(d, 1H); 7.3(m, 2H); 6.7(d, 1H); 6.3(t, 1H); 6.1(d, 1H); 4.8(s, 2H); 3.9(s, 3H); 1.3(m, 1H); 1.05(m, 2H); 0.65(m, 2H). |
| 38 | MeO | H | H | pyrid-3-yl | 8.5(d, 1H); 8.4(s, 1H); 7.9(d, 1H); 7.6(dt, 1H); 7.3(m, 2H); 6.7(d, 1H); 4.9(s, 3H); 3.9(s, 3H); 1.3(m, 1H); 1.1(m, 2H); 0.7(m, 2H). |
| 39 | MeO | H | H | pyrid-4-yl | 82–85° C. |
| 40 | Cl | H | H | CN | 8.5(d, 1H); 7.8(dd, 1H); 7.5(d, 1H); 4.6(s, 2H); 1.3(m, 1H); 1.1(m, 2H); 0.8(m, 2H). |
| 41 | F | H | H | CN | 8.3(d, 1H); 7.9(m, 1H); 7.1(dd, 1H); 4.6(s, 2H); 1.3(m, 1H); 1.1(m, 2H); 0.8(m, 2H). |
| 42 | * | * | * | * | 8.1(d, 1H); 7.8(t, 1H); 7.5(dd, 1H); 6.8(d, 1H); 5.1(d, 2H); 4.0(s, 3H); 1.3(m, 1H); 1.1(m, 2H); 0.7(m, 2H). |
| 43 | F | H | H | cyclopropyl | |
| 44 | Cl | H | H | cyclopropyl | |
| 45 | F | H | H | CH₂F | |
| 46 | F | H | H | CHF₂ | |
| 47 | Cl | H | H | CH₂F | |
| 48 | Cl | H | H | CHF₂ | |
| 49 | F | H | H | CH=CH₂ | |
| 50 | F | H | H | C≡CH | |
| 51 | F | H | H | C≡CMe | |
| 52 | Cl | H | H | C≡CMe | |
| 53 | Cl | H | H | Et | |
| 54 | EtO | H | H | H | |
| 55 | EtO | H | H | Me | |
| 56 | EtO | H | H | CH=CH₂ | |
| 57 | EtO | H | H | C≡CH | |
| 58 | EtO | H | H | C≡CMe | |
| 59 | EtO | H | H | CN | |
| 60 | EtO | H | H | cyclopropyl | |
| 61 | EtO | H | H | CH₂F | |
| 62 | EtO | H | H | CH₂F | |
| 63 | EtO | H | H | Et | |

*Compound No. 42 of Table I has the structure:

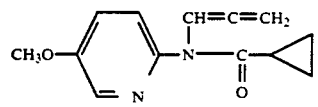

TABLE II

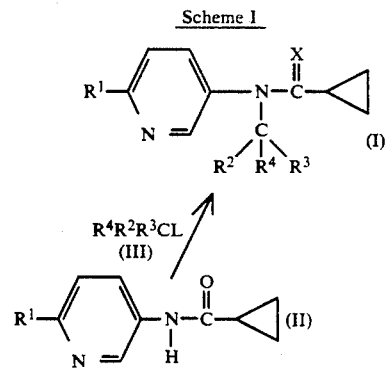

| Compound No | R¹ | R² | R³ | R⁴ | NMR/mp |
|---|---|---|---|---|---|
| 1 | MeO | H | H | CH=CH₂ | 8.0(d, 1H); 7.4(dd, 1H); 6.8(d, 1H); 6.0(m, 1H); 5.2(m, 2H); 4.9(m, 2H); 4.0(s, 3H); 1.6(m, 1H); 1.3(m, 2H); 0.8(m, 2H). |
| 2 | MeO | H | H | H | 8.1(d, 1H); 7.5(dd, 1H); 6.8(d, 1H); 4.0(s, 3H); 3.7(s, 3H); 1.7(m, 1H); 1.3(m, 2H); 0.8(m, 2H). |
| 3 | MeO | H | H | Me | |
| 4 | MeO | H | H | C≡CH | |
| 5 | MeO | H | H | C≡CMe | |
| 6 | MeO | H | H | CN | |
| 7 | MeO | H | H | cyclopropyl | |
| 8 | MeO | H | H | CH₂F | |
| 9 | MeO | H | H | CHF₂ | |
| 10 | MeO | H | H | Et | |

In Table III selected $^{13}C$ data are given for certain compounds. Where these data are given, chemical shifts are in ppm from tetramethylsilane and deuterochloroform was used as solvent.

TABLE III

| Compound No | Data |
|---|---|
| 1 | 173.7 (carbonyl carbon), 162.8, 145.5, 137.6, 134.4, 111.5, 53.8, 37.6, 12.3, 8.4. |
| 33 | 173.8 (carbonyl carbon), 163.0, 146.4, 138.6, 133.2, 111.6, 56.3, 53.7, 26.9, 20.1, 12.7, 8.5. |

In Table IV selected infra red data are given for certain compounds. Where these data are given, absorptions are measured in $cm^{-1}$ and samples were analysed as films between potassium bromide plates.

TABLE IV

| Compound No | Data |
|---|---|
| 18 | 3000, 2940, 1760, 1675, 1615, 1500, 1425, 1390, 1295, 1205, 1030 $cm^{-1}$. |
| 21 | 2930, 1730, 1650, 1485, 1410, 1370, 1280, 1180, 1020 $cm^{-1}$. |
| 22 | 3000, 2940, 1735, 1655, 1600, 1490, 1410, 1275, 1020, 830, 755 $cm^{-1}$. |

The compounds of the invention having the general formula (I), wherein X is oxygen, can be prepared from the amides of general formula (II) as shown in Scheme I.

Throughout Scheme I the terms R¹, R², R³ and R⁴ are as defined above, L is a halogen atom or other good leaving group and X is oxygen.

Thus, compounds of general formula (I) can be prepared by treating the appropriate amide of general formula (II) with an alkylating agent of the general formula (III) and a base (such as potassium hydroxide or sodium hydride) in a suitable solvent (such as dimethyl sulphoxide or dimethylformamide).

The preparation of compounds of general formula (II) is described in the literature (see, for example, EP0243971-A2).

Scheme I

The compounds of formula (I), wherein R² is hydrogen and X is oxygen, can be prepared as shown in Scheme II. Throughout Scheme II the terms R¹, R³ and R⁴ are as defined above, R² is hydrogen and X is oxygen.

Thus, compounds of general formula (I), wherein R² is hydrogen and X is oxygen, can be prepared by treatment of aminopyridines of general formula (IV) with a cyclopropane carboxylic acid chloride of formula (V) in a suitable solvent (such as pyridine) in the presence of a suitable base (such as pyridine).

Compounds of general formula (IV) can be prepared by the reduction of imines of general formula (VI) using a suitable reducing agent (such as sodium borohydride, or hydrogen with a suitable catalyst (such as palladium or platinum)) in a suitable solvent (such as methanol).

Compounds of general formula (VI) can be prepared by the reaction of a suitable aminopyridine of general formula (VII) with an appropriately substituted aldehyde or ketone of general formula (VIII) in a suitable solvent (such as toluene) in the presence of a catalytic amount of a suitable acid (such as p-toluenesulphonic acid) with a suitable dehydrating agent (such as a molecular sieve).

If desired, the last two steps can be carried out in a one-pot process without isolation of the intermediate compounds of general formula(VI).

Scheme II

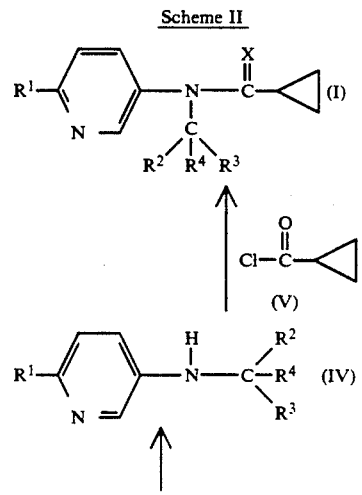

-continued
Scheme II

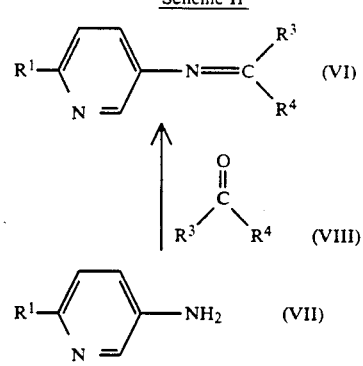

The compounds of the invention having the general formula (I) wherein X is sulphur, can be prepared from compounds of general formula (I), wherein X is oxygen as shown in Scheme III. Throughout Scheme III the terms $R^1$, $R^2$, $R^3$ and $R^4$ are as defined above Scheme III

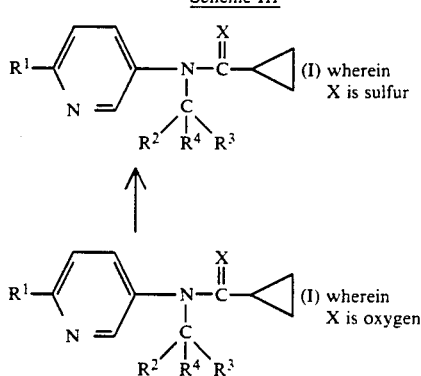

Thus, compounds of general formula (I), wherein X is sulphur, can be prepared by treating an appropriate compound of general formula (I), wherein X is oxygen, with a suitable sulphurating reagent (for example, Lawesson's Reagent or Belleau's Reagent (Tet. Lett. 24(36) 3815–8 (1983))) in a suitable solvent (for example toluene or tetrahydrofuran) at a suitable temperature.

In another aspects the present invention includes the processes described above and the intermediate chemicals of general formulae (VI) and (IV).

The compounds of the invention are active fungicides and may be used to control one or more of the following pathogens: *Pyricularia oryzae* on rice. *Puccinia recondita, Puccinia striiformis* and other rusts on wheat, *Puccinia hordei, Puccinia striiformis* and other rusts on barley, and rusts on other hosts e.g. coffee, pears, apples, peanuts, vegetables and ornamental plants. *Erysiphe graminis* (powdery mildew) on barley and wheat and other powdery mildews on various hosts such as *Sphaerotheca macularis* on hops, *Sphaerotheca fuliginea* on cucurbits (e.g. cucumber), *Podosphaera leucotricha* on apple and *Uncinula necator* on vines. Helminthosporium spp., Rhynchosporium spp., Septoria spp., Pyrenophora spp., *Pseudocercosporella herpotrichoides* and *Gaeumannomyces graminis* on cereals. *Cercospora arachidicola* and *Cercosporidium personata* on peanuts and other Cercospora species on other hosts, for example, sugar beet, bananas, soya beans and rice. *Botrytis cinerea* (grey mould) on tomatoes, strawberries, vegetables, vines and other hosts. Alternaria spp. on vegetables (e.g. cucumber), oil-seed rape, apples, tomatoes and other hosts. *Venturia inaequalis* (scab) on apples. *Plasmopara viticola* on vines. Other downy mildews such as *Bremia lactucae* on lettuce, Peronospora spp. on soybeans, tobacco, onions and other hosts, *Pseudoperonospora humuli* on hops and *Pseudoperonospora cubensis* on cucurbits. *Phytophthora infestans* on potatoes and tomatoes and other Phytophthora spp. on vegetables, strawberries, avocado, pepper, ornamentals, tobacco, cocoa and other hosts. *Thanatephorus cucumeris* on rice and other Rhizoctonia species on various hosts such as wheat and barley, vegetables, cotton and turf.

Some of the compounds show a broad range of activities against fungi in vitro. They may also have activity against various post-harvest diseases of fruit (e.g. *Penicillium digitatum* and italicum and *Trichoderma viride* on oranges, *Gloeosporium musarum* on bananas and *Botrytis cinerea* on grapes).

Further, some of the compounds may be active as seed dressings against pathogens including Fusarium spp., Septoria spp., Tilletia spp., (bunt, a seed-borne disease of wheat), Ustilago spp. and Helminthosporium spp. on cereals, *Rhizoctonia solani* on cotton and *Pyricularia oryzae* on rice.

The compounds may move acropetally/locally in plant tissue. Moreover, the compounds may be volatile enough to be active in the vapour phase against fungi on the plant.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides a fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropyl- naphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10-85%, for example 25-60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2(1H-1,2,4-triazol-1-yl-methyl)butyronitrile, (Z)-N-but-2-enyloxymethyl-2-chloro-2',6'-diethylacetanilide, 1-(2-cyano-2-methoxyiminoacetyl)-3-ethyl urea, 1-[(2RS,4RS;2RS,4RS)-4-bromo-2-(2,4-dichlorophenyl)tetrahydrofurfuryl]-1H-1,2,4-triazole, 3-(2,4-dichlorophenyl)-2-(1H-1,2,4-triazol-1-yl)-quinazolin-4(3H)-one, 3-chloro-4-[4-methyl-2-(1H-1,2,4-triazol-1-methyl)-1,3-dioxolan-2-yl]phenyl-4-chlorophenyl ether, 4-bromo-2-cyano-N,N-dimethyl-6-trifluoromethylbenzimidazole-1-sulphonamide, 5-ethyl-5,8-dihydro-8-oxo(1,3)-dioxolo(4,5-g)quinoline-7-carboxylic acid, α-[N-(3-chloro-2,6-xylyl)-2-methoxyacetamido]-γ-butyrolactone, aldimorph, anilazine, benalaxyl, benomyl, biloxazol, binapacryl, bitertanol, blasticidin S, bupirimate, buthiobate, captafol, captan, carbendazim, carboxin, chlorbenz-thiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-benzyl-N-([methyl(methylthioethylideneamino-oxycarbonyl)amino]thio)-β-alaninate, etridiazole, fenapanil, fenarimol, fenfuram, fenpiclonil, fenpropidin, fenpropimorph, fentin acetate, fentin hydroxide, flutolanil, flutriafol, flusilazole, folpet, fosetyl-aluminium, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepanipyrim, mepronil, metalaxyl, methfuroxam, metsulfovax, myclobutanil, N-(4-methyl-6-prop-1-ynylpyrimidin-2-yl)aniline, neoasozin, nickel dimethyldithiocarbamate, nitrothal-isopropyl, nuarimol, ofurace, organomercury compounds, oxadixyl, oxycarboxin, pefurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, SSF-109, streptomycin, sulphur, tebuconazole, techlofthalam, tecnazene, tetra-conazole, thiabendazole, thicyofen, thiophanate-methyl, thiram, tolclofos-methyl, triacetate salt of 1,1'-iminodi(octa-methylene)diguanidine, triadimefon, triadimenol, triazbutyl, tricyclazole, tridemorph, triforine, validamycin A, vinclozolin, zarilamid and zineb. The compounds of general formula (I) can be mixed with soil, peat or other rooting media for the protection of plants against seedborne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-dimethyl-2-oxo-1,2-dihydropyridine-3-carboxylic acid, methyl-3,6-dichloroanisate, abscisic acid, asulam, benzoyl-prop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following Examples illustrate the invention.

EXAMPLE 1

This Example illustrates the preparation of N-ethyl N-(2-methoxy-5-pyridyl)-cyclopropane carboxamide (Compound No. 2 in Table I).

N-(2-Methoxy-5-pyridyl)-cyclopropane carboxamide (2 g, 0.0104 mol) was added portionwise to a stirred solution of powdered potassium hydroxide (2.3 g, 0.0417 mol) in dimethyl sulphoxide (20 ml) at room temperature. A solution of ethyl bromide (3.25 g, 0.0298 mol) in dimethyl sulphoxide (5 ml) was added dropwise during 2 minutes and the reaction stirred at room temperature for 1 hour.

The reaction mixture was then poured into water (100 ml) and extracted three times with dichloromethane (20 ml). The organic layers were washed four times with water (50 ml), dried, filtered and evaporated under reduced pressure to give N-ethyl N-(2-methoxy-5-pyridyl)cyclopropane carboxamide as a light brown oil (1.31 g).

EXAMPLE 2

This Example illustrates the preparation of N-methyl N-(2-methoxy-5-pyridyl)-cyclopropane carboxamide (compound No. 1 in Table I).

Sodium hydride (0.80 g) was added in one portion to a stirred solution of N-(2-methoxy-5-pyridylcyclopropanecarboxamide (5.4 , 0.03 moles) and dimethyl formamide (100 ml). The reaction was slightly exothermic and a gas was evolved. After stirring for 40 minutes iodomethane (1.8 ml, 0.03 moles) was added over a period of 20 seconds. The reaction was exothermic to 42° C. The reaction was stirred for 2 hours and then diluted with ether (200 ml) and washed with water (150 ml). The ether phase was dried over anhydrous magnesium sulphate and evaporated in vacuo to give 5.7 g of the desired product.

EXAMPLE 3

This Example illustrates the preparation of N-(4-nitrobenzyl)-N-(2-methoxy-5-pyridyl)cyclopropanecarboxamide (Compound No. 16 in Table I).

5-Amino-2-methoxypyridine (12.4 g, 0.10 moles) was added to a stirred mixture of p-nitrobenzaldehyde (15.1 g, 0.10 moles) and methanol (150 ml) under a nitrogen atmosphere. Another solid formed almost immediately on addition of the amine. The reaction was diluted with more methanol (100 ml) and stirred for 45 minutes at room temperature when sodium borohydride (3.8 g, 0.10 moles) was added in 5 portions. The reaction was exothermic and cooling was applied maintaining the temperature at 28° to 30° C. The reaction was stirred at room temperature for 3 hours and then concentrated in vacuo to about 60 ml and then diluted with 5% sodium hydroxide solution (200 ml) and extracted with ether (2×150 ml). The extract was dried over anhydrous magnesium sulphate and evaporated in vacuo to give 24 g of an orange oil (N-(4-nitrobenzyl)-2-methoxy-5-pyridylamine) that crystallized, mp 58° C.59° C.

Cyclopropancarboxylic acid chloride (1.80 ml, 0.02 moles) was added to a solution of N-(4-nitrobenzyl)-2-methoxy-5-pyridylamine (4.7 g, 0.02 moles) in methylene chloride (100 ml). The reaction was washed with 5% sodium bicarbonate solution (2×100 ml); dried over anhydrous magnesium sulphate and evaporated in vacuo to give an oil that was crystallised from hexane to give 4.5 g of the desired product, mp 67° C.-71° C.

EXAMPLE 4

This Example illustrates the preparation of N-methyl-N-(2-methoxy-5-pyridyl)-cyclopropanethiocarboxamide (Compound No. 2 in Table II).

N-Methyl-N-(2-methoxy-5-pyridyl)-cyclopropanecarboxamide (3 g) was dissolved in dry toluene (50 ml) and Lawesson's Reagent (3.5 g) was added to this solution. The solution was heated to reflux for one hour (approximately), cooled and the solution was concentrated under reduced pressure to leave an orange oil. Column chromatography of this oil using 3:1 hexane:ethyl acetate as eluant produced a yellow oil (1.21 g).

EXAMPLE 5

This Example illustrates the preparation of N-allenyl-N-(2-methoxy-5-pyridyl)-cyclopropanecarboxamide (Compound No. 42 in Table I) and N-prop-1-ynyl-N-(2-methoxy-5-pyridyl)-cyclopropanecarboxamide (Compound No. 25 in Table I).

Powdered potassium hydroxide (6.9 g) was stirred in dimethylsulphoxide (20 ml) for one hour after which time N (2-methoxy-5-pyridyl)cyclopropanecarboxamide (6 g) was added. After stirring the resulting mixture for a further hour, propargyl bromide (3 ml) was added dropwise, over 15 minutes, to it. The reaction mixture was then stirred at room temperature for 3 hours after which time it was poured into water (100 ml). The resulting mixture was extracted with dichloromethane (2×100 ml), the organic layers were combined, washed with water (5×100 ml), dried over magnesium sulphate and then evaporated under reduced pressure to leave a brown oil. Column chromatography of this oil using 3:1 hexane:ethyl acetate as eluant produced a yellow oil (1.8 g) [which on analysis was found to be N-allenyl-N-(2-methoxy-5-pyridyl)-cyclopropanecarboxamide] and an orange oil (0.41 g) which on analysis was found to be N-prop-1-ynyl-N-(2-methoxy-5-pyridyl)-cyclopropanecarboxamide].

The following are examples of compositions suitable for agricultural and horticultural purposes which can be formulated from the compounds of the invention. Such compositions form another aspect of the invention. Percentages are by weight.

EXAMPLE 6

An emulsifiable concentrate is made up by mixing and stirring the ingredients until all are dissolved.

| Compound No. 5 of Table I | 10% |
| Benzyl alcohol | 30% |
| Calcium dodecylbenzene-sulphonate | 5% |
| Nonylphenolethoxylate (13 moles ethylene oxide) | 10% |
| Alkyl benzenes | 45% |

EXAMPLE 7

The active ingredient is dissolved in methylene dichloride and the resultant liquid sprayed on to the granules of attapulgite clay. The solvent is then allowed to evaporate to produce a granular composition.

| Compound No. 5 of Table I | 5% |
| Attapulgite granules | 95% |

EXAMPLE 8

A composition suitable for use as a seed dressing is prepared by grinding and mixing the three ingredients.

| Compound No. 5 of Table I | 50% |
| Mineral oil | 2% |
| China clay | 48% |

EXAMPLE 9

A dustable powder is prepared by grinding and mixing the active ingredient with talc.

| Compound No. 5 of Table I | 5% |
| Talc | 95% |

EXAMPLE 10

A suspension concentrate is prepared by ball milling the ingredients to form an aqueous suspension of the ground mixture with water.

| Compound No. 5 of Table I | 40% |
| Sodium lignosulphonate | 10% |
| Bentonite clay | 1% |
| Water | 49% |

This formulation can be used as a spray by diluting into water or applied directly to seed.

EXAMPLE 11

A wettable powder formulation is made by mixing together and grinding the ingredients until all are throughly mixed.

| Compound No. 5 of Table I | 25% |
| Sodium lauryl sulphate | 2% |
| Sodium lignosulphonate | 5% |
| Silica | 25% |
| China clay | 43% |

EXAMPLE 12

The compounds were tested against a variety of foliar fungal diseases of plants. The technique employed was as follows.

The plants were grown in John Innes Potting Compost (No 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:

4 = no disease
3 = trace-5% of disease on untreated plants
2 = 6-25% of disease on untreated plants
1 = 26-59% of disease on untreated plants
0 = 60-100% of disease on untreated plants The results are shown in Tables V, VI and VII.

TABLE V

Data for Compounds in Table I

| Compound No | Puccinia recondita (Wheat) | Erysiphe graminis hordei (Barley) | Venturia inaequalis (Apple) | Pyricularia oryzae (Rice) | Cercospora arachidicola (Peanut) | Plasmopara viticola (Vine) |
|---|---|---|---|---|---|---|
| 1 | 4 | 4 | 4 | 0 | 2 | 4 |
| 2 | 4 | 4 | 4 | 0 | 3 | 0 |
| 3 | 4 | 4 | 4 | 0 | 3 | 0 |
| 4 | 4 | 4 | 4 | | | 4 |
| 5 | 0 | 2 | 4 | 0 | 3 | 4 |
| 6 | 4 | 4 | 3* | 0 | | 0* |
| 7 | 4 | 4 | 4 | 0 | 2 | 0 |
| 8 | 4 | 4 | 4 | 0 | 2 | 0 |
| 10 | 0 | 0 | 2 | 0 | 2 | 0 |
| 11 | 0 | 2 | 0 | 2 | 0 | 0 |
| 13 | 0 | 4 | 4 | 0 | 0 | 0 |
| 14 | 2 | 4 | 0 | 0 | 0 | 0 |
| 15 | 3 | 1* | 4 | 0 | 0 | 4 |
| 16 | 0 | 3 | 3 | 0 | 0 | 0 |
| 17 | | 3 | 4 | 0 | | 2 |
| 19 | 4 | 4 | 0 | 0 | | 0 |
| 23 | 4 | 4 | 4 | 0 | | 0 |
| 24 | 4 | 4 | 4 | 0 | | 0 |
| 25 | 4 | 4 | 0 | 0 | | 0 |
| 26 | 4 | 4 | 4 | 0 | | 0 |
| 27 | 4 | 3 | 4 | 0 | | 0 |
| 29 | 3 | 4 | 4 | 0 | | 0 |
| 30 | 4 | 3 | 0 | 2 | | 0 |
| 31 | | 3 | 4 | 0 | | 0 |
| 32 | 4 | 2 | 4 | 0 | | 4 |
| 33 | 4 | 4 | 4 | 0 | | 1 |
| 34 | 4 | 4 | 4 | 0 | | 0 |
| 35 | 0 | 3 | 0 | 0 | | 0 |
| 36 | 0 | 3 | 3 | 3 | | 0 |
| 37 | 0 | 4 | 0 | 2 | | 0 |
| 38 | 0 | 4 | 4 | 0 | 0 | 0 |
| 39 | 0 | 3 | 4 | 0 | 0 | 0 |

*Compounds tested at 25 ppm only

TABLE VI

Data for Compounds in Table I

| Compound No | Puccinia recondita (Wheat) | Erysiphe graminis tritici (Wheat) | Venturia inaequalis (Apple) | Pyricularia oryzae (Rice) | Septoria nordorum | Plasmopara viticola (Vine) | Phytophthora infestans (Tomato) |
|---|---|---|---|---|---|---|---|
| 28 | 4 | 4 | 3 | 2 | 4 | 0 | 1 |
| 40 | 0 | 3 | 0 | 0 | 0 | 0 | 0 |
| 41 | 3 | 4 | 0 | 0 | 0 | 0 | 0 |
| 42 | 4 | 3 | 4 | 0 | 2 | 0 | 0 |

TABLE VII

Data for Compounds in Table II

| Compound No | Puccinia recondita (Wheat) | Erysiphe graminis tritici (Wheat) | Venturia inaequalis (Apple) | Pyricularia oryzae (Rice) | Septoria nordorum | Plasmopara viticola (Vine) | Phytophthora infestans (Tomato) |
|---|---|---|---|---|---|---|---|
| 1 | 4 | 0 | 1 | 0 | 0 | 0 | 0 |
| 2 | 4 | 4 | 3 | 0 | 0 | 0 | 0 |

We claim:

1. A compound of general formula (I):

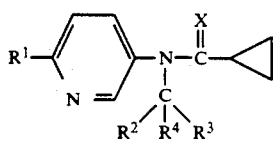

and optical isomers thereof, wherein X is oxygen or sulphur; $R^1$ is halogen, $C_{1-4}$ alkoxy or $C_{1-4}$ haloalkoxy; $R^2$ and $R^3$, which are the same or different, are hydrogen, $-CO_2R^5$ or $C_{1-4}$ alkyl; $R^4$ is hydrogen, cyano, $C_{1-4}$ alkyl optionally substituted with cyano or halogen, $-(CH_2)_nCO_2R^6$, $-CONR^6R^7$, $C_{3-6}$ cycloalkyl, $C_{2-4}$ alkenyl, $C_{2-4}$ alkynyl, optionally substituted phenyl or optionally substituted 5- or 6-member heteroatomatic ring containing a sulfur, oxygen or 1 or 2 nitrogen atoms the optional substituents on the phenyl and heteroaromatic moieties include $C_{1-4}$ alykl, $C_{1-4}$ haloalkyl, $C_{1-4}$ alkoxy, $C_{1-4}$ haloalkoxy, $C_{1-4}$ alkoxy $(C_{1-4})$ alkyl, halogen, nitro, cyano, amino, mono- or di-$(C_{1-4})$ alkylamino, $CO_2R^8$, $COR^8$, $SO_2R^9$ and hydroxy; $R^8$ is hydrogen, $C_{1-4}$ haloalkyl or phenyl optionally substituted with halogen, $C_{1-4}$ al alkyl, $C_{1-4}$ haloalkyl, $C_{1-4}$ alkoxy or $C_{1-4}$ haloalkoxy; $R^9$ is $C_{1-4}$ alkyl, $C_{1-4}$ haloalkyl or phenyl optionally substituted with halogen, $C_{1-4}$ alkyl, $C_{1-4}$ haloalkyl, $C_{1-4}$ alkoxy or $C_{1-4}$ haloalkoxy; or the group $CR^2R^3R^4$ can form an allene moiety optionally substituted with $C_{1-4}$ alkyl; $R^5$, $R^6$ and $R^7$, which are the same or different, are hydrogen or $C_{1-4}$ alkyl; n is 0, 1, 2, 3 or 4; and metal complexes thereof.

2. A compound as claimed in claim 1 having the general formula (I):

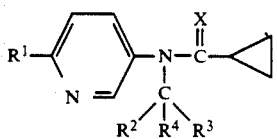

wherein X is oxygen or sulphur; $R^1$ is halogen, $C_{1-4}$ alkoxy or $C_{1-4}$ haloalkoxy; $R^2$ and $R^3$ are both hydrogen; $R^4$ is hydrogen, cyano, $C_{1-4}$ alkyl optionally substituted with cyano or halogen, $C_{3-6}$ cycloalkyl, $C_{2-4}$ alkenyl, C2-4 alkynyl, optionally group $CR^2R^3R^4$ can form an allene moiety optionally substituted with $C_{1-4}$ alkyl.

3. A compound as claimed in claims 1 or 2 having the general formula (I):

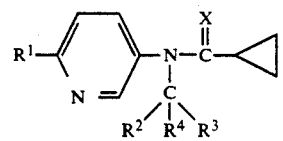

wherein X is oxygen or sulphur; $R^1$ is halogen or $C_{1-4}$ alkoxy; $R^2$ and $R^3$ are both hydrogen; and $R^4$ is hydrogen, cyano, $C_{1-4}$ alkyl optionally substituted with cyano or halogen, $C_{2-4}$ alkenyl or $C_{2-4}$ alkynyl.

4. A compound as claimed in claims 1 or 2 having the general formula (I):

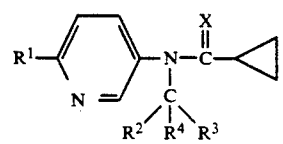

wherein X is oxygen; $R^1$ is $C_1$ alkoxy; $R^2$ and $R^3$ are both hydrogen, and $R^4$ is hydrogen, cyano, $C_{1-4}$ alkyl optionally substituted with cyano or halogen, $C_{2-4}$ alkenyl or $C_{2-4}$ alkynyl.

5. A compound as claimed in claims 1 or 2 having the general formula (I):

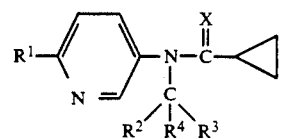

wherein X is oxygen; $R^1$ is methoxy; $R^2$ and $R^3$ are both hydrogen; and $R^4$ is hydrogen, cyano, $C_{1-2}$ alkyl optionally substituted by fluorine or cyano, vinyl ethynyl or prop-1-ynyl.

6. A fungicidal composition comprising a fungicidally effective amount of a compound according to claim 1 and a fungicidally acceptable carrier or diluent therefor.

7. A method of combating fungi which comprises applying to plants, to the seeds of plants or to the locus of the plants or seeds, a compound according to claim 1 or a composition according to claim 6.

* * * * *